United States Patent
Wolf (10) Patent No.: US 7,435,229 B2
(45) Date of Patent: Oct. 14, 2008

(54) SYSTEM FOR TRANSCUTANEOUS MONITORING OF INTRACRANIAL PRESSURE (ICP) USING NEAR INFRARED (NIR) TELEMETRY

(76) Inventor: Erich W. Wolf, 721 Bayou Pines East, Lake Charles, LA (US) 70601

( * ) Notice: Subject to any disclaimer, the term of this patent is extended or adjusted under 35 U.S.C. 154(b) by 51 days.

(21) Appl. No.: 11/065,428

(22) Filed: Feb. 24, 2005

(65) Prior Publication Data

US 2005/0187488 A1    Aug. 25, 2005

Related U.S. Application Data

(60) Provisional application No. 60/582,337, filed on Jun. 23, 2004, provisional application No. 60/577,807, filed on Jun. 8, 2004, provisional application No. 60/547,691, filed on Feb. 25, 2004.

(51) Int. Cl.
*A61B 5/00* (2006.01)

(52) U.S. Cl. .......................... 600/561; 600/486; 73/722

(58) Field of Classification Search ......... 600/300–301, 600/310, 433–435, 473, 561, 485–488; 604/9, 604/164.1, 466, 508–510, 528, 544; 607/33, 607/60; 73/722

See application file for complete search history.

(56) References Cited

U.S. PATENT DOCUMENTS

| | | | |
|---|---|---|---|
| 3,488,821 A * | 1/1970 | Richards | 29/25.35 |
| 3,672,352 A * | 6/1972 | Summers | 600/476 |
| 4,354,506 A | 10/1982 | Sakaguchie et al. | |
| 4,385,636 A | 5/1983 | Cosman | |
| 4,471,786 A | 9/1984 | Inagaki et al. | |
| 4,550,611 A * | 11/1985 | Czarnocki | 73/708 |
| 4,653,508 A | 3/1987 | Cosman | |
| 4,660,568 A | 4/1987 | Cosman | |
| 4,677,982 A * | 7/1987 | Llinas et al. | 600/473 |
| 5,704,352 A | 1/1998 | Tremblay et al. | |
| 5,741,246 A * | 4/1998 | Prescott | 606/7 |
| 5,873,840 A | 2/1999 | Neff | |
| 6,083,174 A | 7/2000 | Brehmeier-Flick et al. | |
| 6,113,553 A | 9/2000 | Chubbick | |
| 6,162,238 A | 12/2000 | Kaplan et al. | |
| 6,164,284 A * | 12/2000 | Schulman et al. | 128/899 |
| 6,243,608 B1 * | 6/2001 | Pauly et al. | 607/60 |
| 6,442,413 B1 | 8/2002 | Silver | |
| 6,529,759 B1 | 3/2003 | Tucker et al. | |

(Continued)

*Primary Examiner*—Max Hindenburg
*Assistant Examiner*—Rene Towa
(74) *Attorney, Agent, or Firm*—Schultz & Associates, P.C.

(57) ABSTRACT

A system for measuring and converting to an observer intelligible form an internal physiological parameter of a medical patient. The invention allows transcutaneous telemetry of the measured information intracranial pressure via a system which includes a patient implanted sensor module and a processing and display module which is external of the patient and optically coupled to the sensor module via an external coupling module. A sensor within the implanted module transduces the measured information and a near infrared (NIR) emitter transmits this telemetry information when interrogated by the complementary external coupling module. Power for the sensor module is derived inductively through rectification of a transcutaneously-applied high-frequency alternating electromagnetic field which is generated by a power source within the external coupling module, in concept much like a conventional electrical transformer. A computer within the processing and display module calculates the parameter value from the NIR telemetry signal and represents this data either in numerical, graphical, or analog format.

12 Claims, 9 Drawing Sheets

U.S. PATENT DOCUMENTS 6,533,733 B1 * 3/2003 Ericson et al. .............. 600/561
6,610,096 B2    8/2003 MacDonald
2005/0143790 A1  6/2005 Kipke et al.
2005/0158356 A1  7/2005 Hunter et al.

* cited by examiner

SYSTEM FOR TRANSCUTANEOUS MONITORING OF INTRACRANIAL PRESSURE (ICP) USING NEAR INFRARED (NIR) TELEMETRY

RELATED APPLICATIONS

This application claims priority from U.S. Provisional Applications 60/547,691 filed Feb. 25, 2004; 60/577,807 filed Jun. 8, 2004; and 60/582,337 filed Jun. 23, 2004.

FIELD OF INVENTION

This invention relates generally to transcutaneous telemetry with an implantable biomedical device, and more specifically relates to a system for transcutaneous monitoring of intracranial pressure (ICP).

BACKGROUND OF THE INVENTION

The measurement of intracranial pressure (ICP) plays a critical role in several neurosurgical conditions. Various pathological processes such as hydrocephalus, tumors, and trauma can cause alterations in the pressure within the skull. If not adequately controlled, increases in intracranial pressure (due to accumulation of cerebrospinal fluid, blood clots, tumors, or brain swelling) can cause secondary damage to otherwise healthy brain tissue.

A number of technologies currently exist to monitor brain pressure. Many of these rely on invasive techniques with percutaneously implanted sensors. Wires or fiber optic cables are often used to transduce pressure information from electromechanical or optomechanical transducers, which relegates these technologies to short term use. At the end of use these sensors are withdrawn from the body. Several disadvantages are associated with such devices: 1) the presence of a percutaneous probe increases the chance of iatrogenic infections such as meningitis and cerebritis; 2) the probe must be withdrawn at the end of use and so it is not reusable for subsequent episodes of suspected intracranial hypertension such as with hydrocephalus; and 3) the percutaneous cable is subject to mechanical failure and to inadvertent pull-out during routine patient care.

In an attempt to mitigate these disadvantages, numerous investigators have tried to develop non-invasive techniques for monitoring intracranial pressure. Such methods have employed mathematical correlations between physiological variables which can be transduced extracorporally such as blood pressure, heart rate, Doppler ultrasound of cerebral blood vessels, near-infrared (NIR) spectroscopy of cerebral oxygenation, retinal imaging, etc. While some success has been achieved in monitoring trends in ICP, no method has been fully successful in deriving the absolute intracranial pressure, and these known techniques have not gained significant clinical utility for monitoring ICP.

SUMMARY OF INVENTION

The present invention allows ad lib transcutaneous telemetry of absolute intracranial pressure via a system which includes a patient implanted sensor module and a processing and display module which is external of the patient and optically coupled to the sensor module via an external coupling module. The sensor module is implanted in much the same fashion as with existing technologies but the skin is closed back over the device and no cabling penetrates the skin. A sensor within the implanted module transduces absolute pressure information and a near infrared (NIR) emitter transmits this telemetry information when interrogated by the complementary external coupling module. Light in the near-infrared spectrum is easily transmitted through the skin and is detected by the external module. Indefinite longevity and small size is attained in the implant by not incorporating a power source within the module. Instead, power is derived inductively through rectification of a transcutaneously-applied high-frequency alternating electromagnetic field which is generated by a power source within the external coupling module, in concept much like a conventional electrical transformer. A computer within the processing and display module calculates the absolute pressure from the NIR telemetry signal and represents this data either in numerical, graphical, or analog format.

The present invention overcomes the aforementioned disadvantages of existing technologies by providing a means for telemetric conveyance of physiological data via transcutaneous projection of a near infrared light beam. The use of this technique for telemetry of intracranial pressure is only one of many potential applications and any reference to intracranial pressure monitoring is not meant to limit the scope of applicability. Furthermore, the transcutaneous telemetry of information is not limited to a unidirectional fashion. Indeed, telemetric data may be transferred bi-directionally between an extra corporeal device and an implanted device. Broadly stated, the implanted device may be a sensor of one or more physiological parameters, contain some form of data unique to the device or unique to the person (or organism) harboring the implant, or may somehow monitor the physiological state of the person (or organism). Specific examples of devices include, but are not limited to, intracranial pressure monitors, tissue oxygen sensors, glucose sensors, neurostimulators, pacemakers, and defibrillators. An extra corporeal device allows recording, display, or interpretation of data from the implanted device and may communicate in bi-directional fashion to convey information back to the implant such as calibration data, handshaking data, etc.

Feasibility of Transcutaneous Data Communication Using Near Infra-Red:

Physiological parameters such as tissue oxygenation may be measured by comparing the absorption of specific optical wavelengths by the hemoglobin and cytochrome chromophores. This technology is ubiquitous in the hospital setting in the form of pulse oximetry. In what is best disclosed as spectrophotometry, these aforementioned measurement techniques utilize analog means to derive quantitative measures of some physiological parameter via absorption of selected spectra. In a dramatic paradigm shift, the presently described invention utilizes an infrared beam to traverse biological tissue for the digital transmission of data.

The suitability of transmission of data across biological tissues via infrared beam is dependent primarily upon the attenuation of the light beam. From the modified Beer-Lambert equation [1], the attenuation, expressed in optical density, is:

$$\text{Attenuation}(OD) = -\log(I/Io) = B\mu_a d_p + G$$

Where I is the transmitted light intensity, Io is the incident intensity, B is a path length factor dependent upon the absorption coefficient $\mu_a$ and scattering coefficent $\mu_s$, $d_p$ is the interoptode distance, and G is an unknown geometry-dependent factor.

The Near Infrared (NIR) spectrum is defined as 750-2500 nm. In vivo measurements of NIR absorption during transillumination of the newborn infant brain [7] suggest an optical density of 10 over interoptode distances of 8-9 cm. Assuming the light source and detector are collinear and antiparallel, the geometry-dependent factor, G, becomes negligible. Because biological tissue is an effective multiple scatterer of light, the effective path length traveled by a given photon can only be estimated. In a study measuring the water absorption peak at 975 nm and assuming an average tissue water content, the path length of brain tissue is estimated at 4.3 times the interoptode distance [4]. Thus, from the Beer-Lambert equations, the calculated absorption coefficient for human brain is approximately 0.26 cm$^{-1}$ with an assumed path length of 4.3 [4]. This is within the range of absorption coefficients (0.0434-0.456 cm$^{-1}$) quoted in the literature [2]. In the studies of Tamura and Tamura [3], extracranial structures such as skin, muscle and bone had minimal effects on the NIR transmission-mode absorbance, presumably because the blood flow and oxygen consumption of these structures is low compared to that of cerebral cortex. The relatively minor contribution of scalp tissue to NIR absorption is further corroborated by Owen-Reece, et al [6]. Thus, it is reasonable to expect that for a typical scalp thickness of 1 cm, the absorption would be somewhat less than: $B\mu_a d_p = (4.3)(0.26)(1) = 1.1$, assuming that the geometry factor is negligible. Therefore, with an attenuation of one to two orders of magnitude and an NIR emitter output power of 5 mW, the transmitted light intensity is well within the sensitivity range of common silicon photodiodes (0.55 A/W, typical).

Delpy, et al [1] have investigated the relationship between attenuation and the transit time of light through tissue in an attempt to determine optical path length. Temporal dispersion resulting from spatial and temporal delta functions of the input beam as it passes through scattering tissue may be described by the temporal spread point function (TSPF) [1]. Using a Monte Carlo model of light transport in tissue and experimentally derived (in vitro rat brain) scattering phase function at 783 nm, they computed the TSPF for a beam of light passing through a 1 cm thick slab of brain tissue. Estimates of path length based upon the time-of-flight of photons using the TSPF integrated over the exit surface, at all exits angles, and assuming radial symmetry, yields an average path length of 5.3 times the interoptode distance [1]. The final photons to emerge from the tissue are calculated to have traveled 9.2 times the interoptode distance [1]. The temporal dispersion of the light will limit the maximum transmission bandwidth:

$$F_{max} = 1/t = c/dn$$

Where $F_{max}$ is the maximum transmission frequency, t is the time for the light to traverse the tissue, c is the speed of light, d is the distance traveled, and n is the refractive index. For a path length of 9.2 cm and a refractive index for tissue of 1.4 [1], $F_{max}$ is 2.33 GHz.

Choice of the preferred NIR wavelength for transcutaneous telemetry pursuant to the present invention is dependent upon the absorption coefficients of the intervening tissues. The absorption by melanosomes dominates over the visible and near-infrared spectra to about 1100 nm, above which free water begins to dominate. Absorption by the dermis decreases monotonically over the 700-1000 nm range. Whole blood has a minimum absorption at about 700 nm but remains low over the 700-1000 nm range. The nadir in the composite absorption spectrum therefore lies in the 800-1000 nm range.

The actual wavelength utilized is therefore dictated by the optimal spectral range (as above) and the availability of suitable semiconductor emitters. Several suitable wavelengths may include, but are not limited to: 760 nm, 765 nm, 780 nm, 785 nm, 790 nm, 800 nm, 805 nm, 808 nm, 810 nm, 820 nm, 830 nm, 840 nm, 850 nm, 870 nm, 880 nm, 900 nm, 904 nm, 905 nm, 915 nm, 920 nm, 940 nm, 950 nm, 970 nm, and 980 nm. Wavelengths outside this range may be used but will be subject to greater attenuation by the intervening tissues.

BRIEF DESCRIPTION OF DRAWINGS

The invention is diagrammatically illustrated, by way of Example, in the drawings appended hereto, in which.

DESCRIPTION OF PREFERRED EMBODIMENTS

Overview of the Preferred Embodiment

Figure 1:
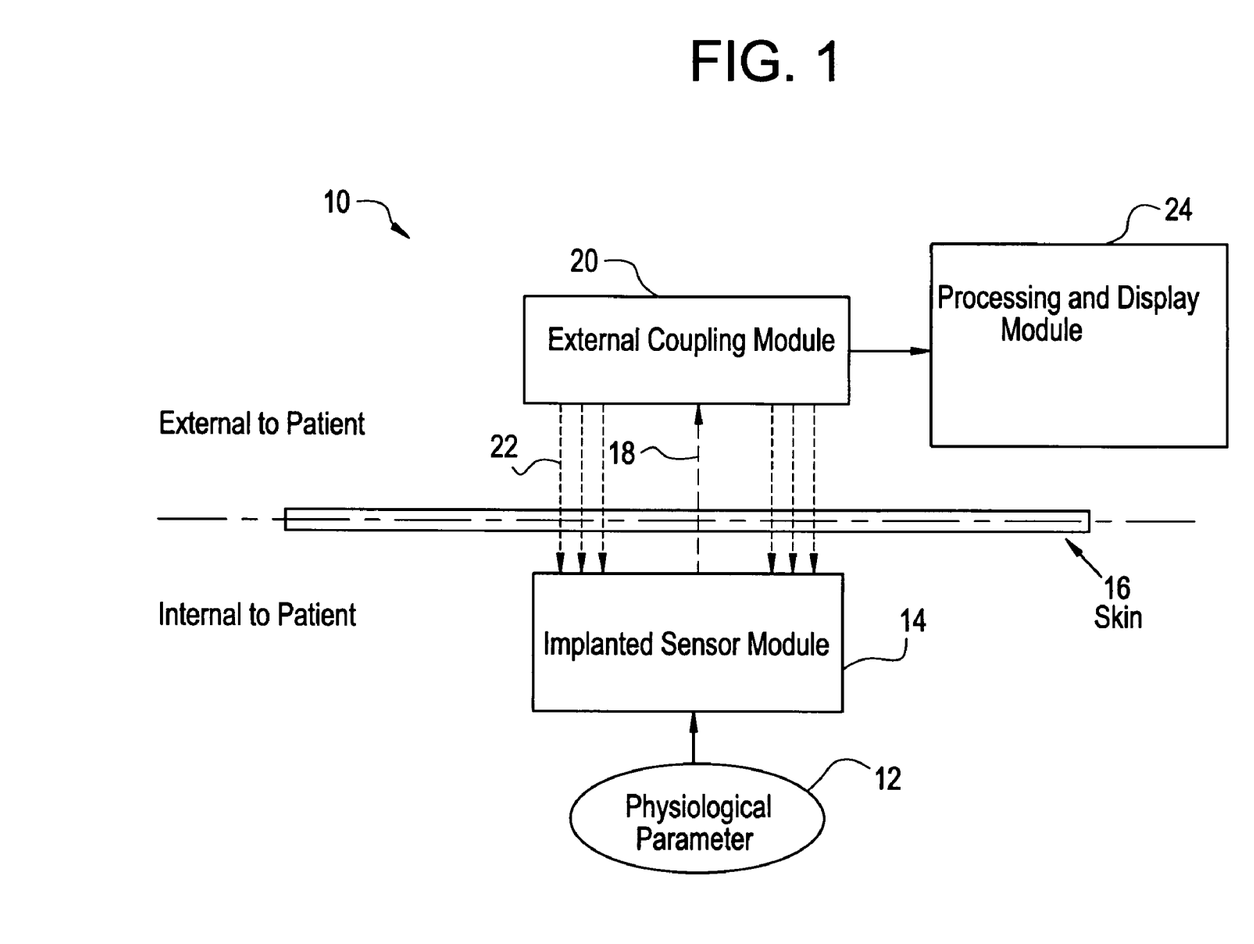
FIG. 1 is a schematic block diagram of a transcutaneous monitoring system in accordance with the present invention.

A schematic block diagram of a transcutaneous monitoring system 10 in accordance with the invention is depicted in FIG. 1. A physiological parameter 12, such as intracranial pressure, is transduced by an implanted sensor module 14. The implant is buried beneath the skin 16 of the patient. Information regarding the transduced physiological parameter 12 is converted to a digital form which modulates a near-infrared (NIR) emitter in the implanted sensor module 14. The modulated NIR light beam 18 emanates from the implanted sensor module 14, permeates the skin 16 of the patient, and is detected by an external coupling module 20. Power to the implanted sensor module 14 is derived inductively through rectification of a transcutaneously-delivered time-varying electromagnetic field 22 which is applied by an external power source via external coupling module 20, in concept much like a conventional electrical transformer. Implanted sensor module 14 is powered only when in the vicinity of the external coupling module 20. A computer within the processing and display module 24 calculates the physiological parameter 12 from the NIR telemetry signal 18 and represents these data either in numerical, graphical, or analog format.

Figure 2:
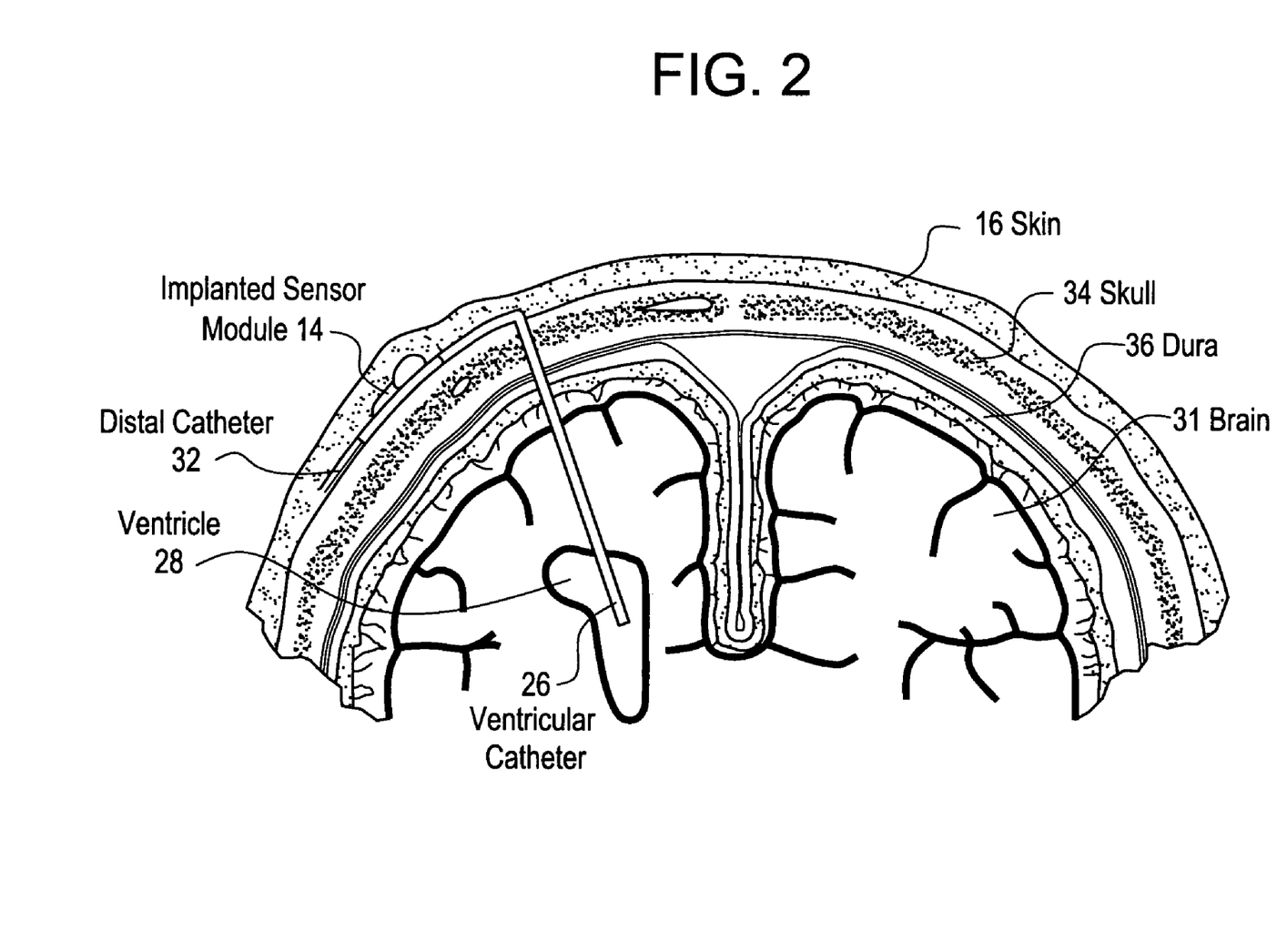
FIG. 2 is simplified longitudinal cross sectional diagram illustrating how the sensor module may be implanted in a typical use with a patient.

A typical in vivo implementation is shown in the simplified longitudinal cross-sectional diagram of FIG. 2. A hollow ventricular catheter 26 is placed surgically into a cerebrospinal fluid (CSF) filled ventricle 28 of the brain 31. The CSF is communicated via the ventricular catheter 26 to the implanted sensor module 14. The physiological parameter 12, intracranial pressure, is sensed and transmitted via infrared telemetry 18 from the implanted sensor module 14, to the external coupling module 20, through the overlying skin 16. In the scenario of a ventriculoperitoneal shunt, the CSF exits the implanted sensor module 14 and passes, via a distal catheter 32, through a valve assembly (not shown) and ultimately to the peritoneal cavity of the abdomen (not shown). The implanted sensor module 14 is installed superficial to, or embedded within, the skull 34. Dura 36 is depicted as an additional anatomical landmark.

Figure 3:
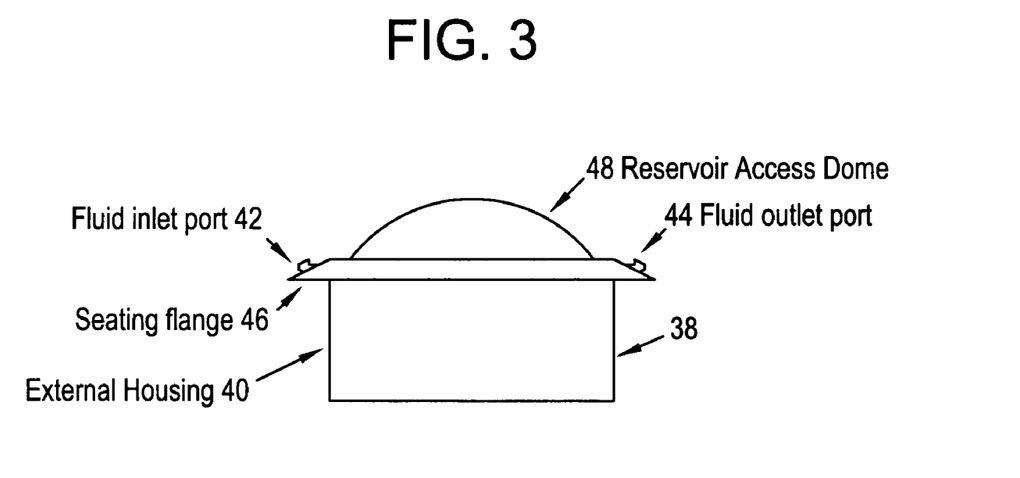
FIG. 3 is a simplified side elevational view of an implanted sensor module in accordance with the invention.
Figure 3A:
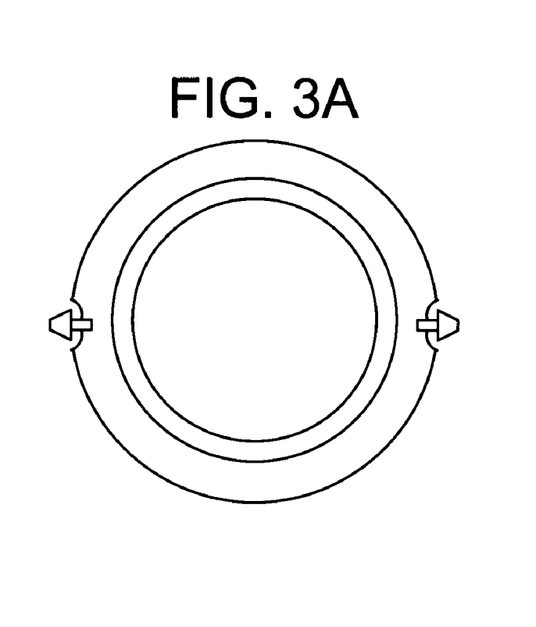
FIG. 3A is top plan view of the device of FIG. 3.

Various designs for the implanted sensor module 14 housing are suitable and a representative design is depicted in FIGS. 3 and 3A which respectively depict simplified side elevational and top plan views of the device 38. Device 38 includes a cylindrical external housing 40 having a fluid inlet port 42 and fluid outlet port 44 for cerebral spinal fluid (CSF). The external housing 40 must be biocompatible, rigid, and have a superficial face which is substantially transparent to near-infrared light 18. A material such as polycarbonate (optically transparent to near infrared wavelengths) may be used.

The footprint of the implant in the preferred embodiment is round to accommodate the implant's power supply coil. Furthermore, a round footprint allows the external housing 40 to be easily recessed into the skull 34 during implantation using a twist-drill. The seating flange 46 limits the depth of the recess such that the seating flange 46 remains flush with the skull 34 surface.

The preferred embodiment may include a reservoir access dome 48, or "Rickham reservoir," which is an integrated self-sealing chamber made of a material such as Silastic. A needle may be introduced percutaneously through the skin 16 into the reservoir access dome 48 to allow access to cerebrospinal fluid within the implanted sensor module 14, which in turn, communicates with cerebrospinal fluid within the brain ventricle 28 via fluid inlet port 42 and ventricular catheter 26. Alternate embodiments of the external housing 40 may include alternative locations for the fluid ports, such as placement of the fluid inlet port 42 on the bottom of external housing 40.

Figure 4:
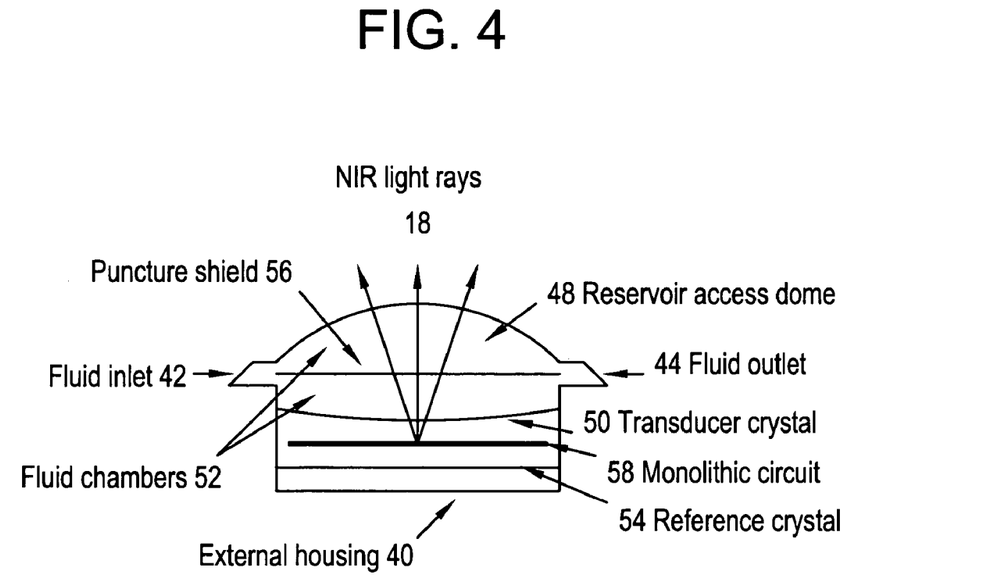
FIG. 4 is a schematic longitudinal cross sectional view of the implanted sensor module.

A schematic longitudinal cross sectional view of the implanted sensor module 14 appears in FIG. 4. Cerebrospinal fluid enters fluid chambers 52 via fluid inlet 42. A transducer crystal 50 is mounted across external housing 40 to act as a diaphragm in contact with fluid chamber 52. In the preferred embodiment, the transducer 50 is a quartz (silicon dioxide) crystal which exhibits a change in oscillation frequency as a predictably stable function of deformation, and hence pressure, on transducer 50. In FIG. 4 the transducer crystal 50 is depicted in the deformed state. The transducer crystal 50 may be composed of a biocompatible material (e.g. silicon dioxide) which will not significantly degrade in mechanical properties over the lifetime of the implant. Important characteristics of the sensor to be employed are sensitivity, electromechanical stability, absolute pressure accuracy, biocompatibility and electrical noise immunity. The quartz crystal transducer element 50 may be trimmed at the factory during fabrication to achieve calibration.

A reference crystal 54 is also housed within the implanted sensor module 14. This reference crystal 54 is of identical construction to that of transducer crystal 50 and the difference in oscillation frequency between these crystals correlates directly with the deformation, and hence, pressure applied to the transducer crystal 50.

A monolithic circuit 58 within the implanted sensor module 14 contains the necessary electronics to operate the implanted sensor module. These electronics act to modulate the output of a near-infrared emitter as a function of pressure on the transducer crystal 50.

A puncture shield 56 serves to protect transducer crystal 50 from damage due to needles introduced through the reservoir access dome 48. The puncture shield 56 as well as the crystal 50 are substantially transparent to the NIR light 18.

Transcutaneous telemetry from the implanted sensor module 14 is transmitted optically to the external coupling module 20 via NIR light 18. In vivo, soft tissues are relatively permeable to wavelengths within the near infrared (NIR) spectrum. This permeability, coupled with specific hemoglobin absorption peaks, is exploited in non-invasive transcutaneous oxygenation monitors and NIR spectroscopy. In these applications it is the relative absorption at specific wavelengths that is capitalized upon, rather than the transmission of data over a tissue-permeable wavelength as in the present invention.

Analog signal transmission is not suitable due to the unpredictability of the NIR absorption by the overlaying tissues 16. However, any one of numerous methods for digital signal transmission may be incorporated. Existing serial data transmission protocols, whether synchronous or asynchronous, require complex electronics to encode the data. More simply, frequency modulation or pulse-width modulation may be employed, particularly since the bandwidth of the physiological data is low. In the preferred embodiment, frequency modulation is used.

A computer within the processing and display module 24 calculates the physiological parameter 12 from the NIR telemetry signal 18, as detected by external coupling module 20, and represents these data either in numerical, graphical, or analog format.

Detailed Description of the Preferred Embodiment

Implanted Sensor Module:

The preferred embodiment of the invention employs a pressure transducer 50 composed of an x-cut quartz crystal. In typical transducer applications, mechanical deformations of a crystal are detected as piezoelectric charges developed across the face of the crystal. While this works well for time-varying signals, leakage currents render this technique inapplicable to measurement of static or slowly-changing deformations of a crystal.

An alternate approach is to resonate an x-cut crystal at its fundamental frequency; mechanical deformation of the crystal, such as due to an applied pressure, will alter the resonant frequency in a predictable fashion. The pressure applied to the crystal face is thus calculated by measuring the change in crystal oscillation frequency. This technique is applicable to both static and dynamic measurements and is extremely stable as a function of time.

The sensitivity of a crystal acting as a pressure-sensitive diaphragm is dependent upon its stiffness and mounting configuration. To achieve maximal sensitivity, the crystal should be as thin as possible, yet adequately robust to withstand the pressure requirements of the application without exceeding the crystal's burst pressure.

The pressure transducer crystal 50 is in contact with cerebrospinal fluid within the fluid chamber 52. The chemical composition of quartz (silicon dioxide) has been demonstrated to be biocompatible and have minimal biofouling (*Biomaterials* 24 [2003]: 1959-67). Biofouling is further minimized by surface polishing of the crystal surface during manufacturing. Long-term resonant frequency stability is theoretically ensured despite biofouling due to the flexural stiffness of the crystal being orders of magnitude greater than that of surface contaminant proteins.

Figure 5:
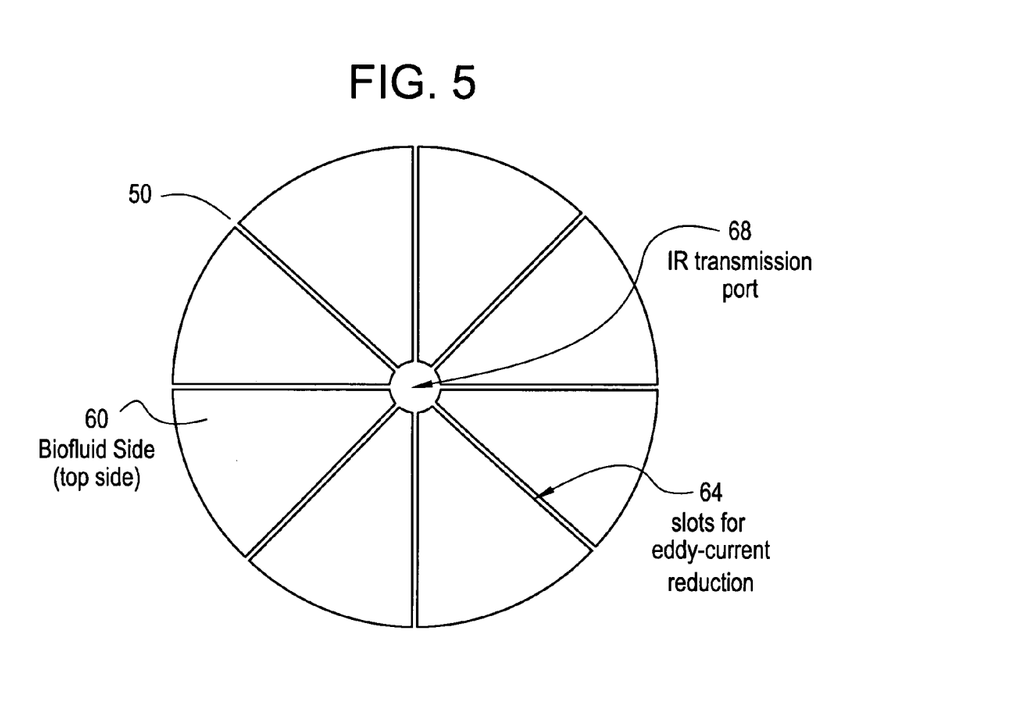
FIG. 5 is a plan view of the upper side of a crystal which may be used in the implant module of the present invention.
Figure 5A:
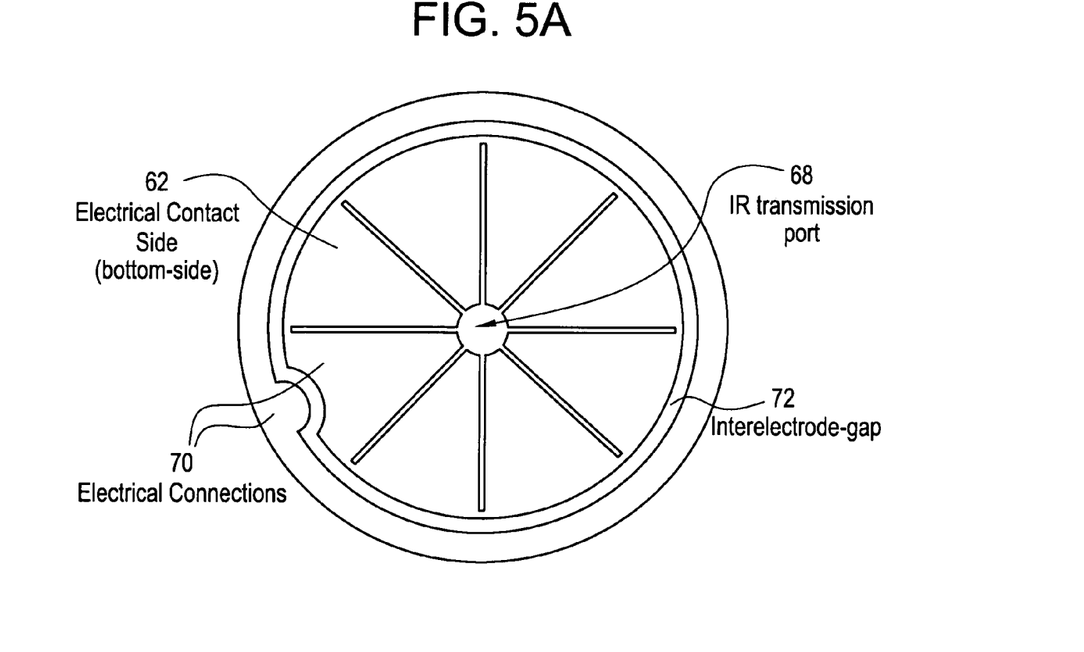
FIG. 5A is a plan view of the lower side of the crystal shown in FIG. 5.

In the preferred embodiment, a gold (Au) coaxial electrode pattern is atomic-sputtered onto the crystal as shown in FIGS. 5 and 5A, which are respectively top 60 and bottom 62 plan views of the crystal. The top side is the biofluid side; the bottom-side 62 is where electrical contact is made. Gold has also been demonstrated to be biocompatible and have minimal biofouling. By lapping gold around the edge from the top 60 to the undersurface at bottom 62 of the crystal, the surface at 60 in contact with the cerebrospinal fluid can be made entirely referenced at ground potential. No electrical connections 70 are in contact with the CSF as electrodes from each face of the crystal are available on the undersurface 62 of the crystal and are separated by an inter-electrode gap 72. Slots 64 may be etched in the gold electrode surface to reduce or prohibit eddy currents from forming, hence improving power coupling from the external coupling module 20 to the implanted sensor module 14. Additionally, an IR transmission port 68 may be left without metallization to allow transmission of infrared light through the crystal.

Pressure on the transducer crystal 50 will cause the oscillation frequency to decrease. Consequently, to ensure a monotonic increase in differential frequency with increasing pressure, it is necessary for nominally identical transducer crystal 50 and reference crystal 54 to be matched such that the transducer crystal 50 has the lower natural frequency of the pair. Alternatively, the transducer crystal 50 may be designed to be nominally lower in frequency than the reference crystal 54 to increase the temporal resolution of the system, but at the expense of immunity to frequency drift.

Figure 6:
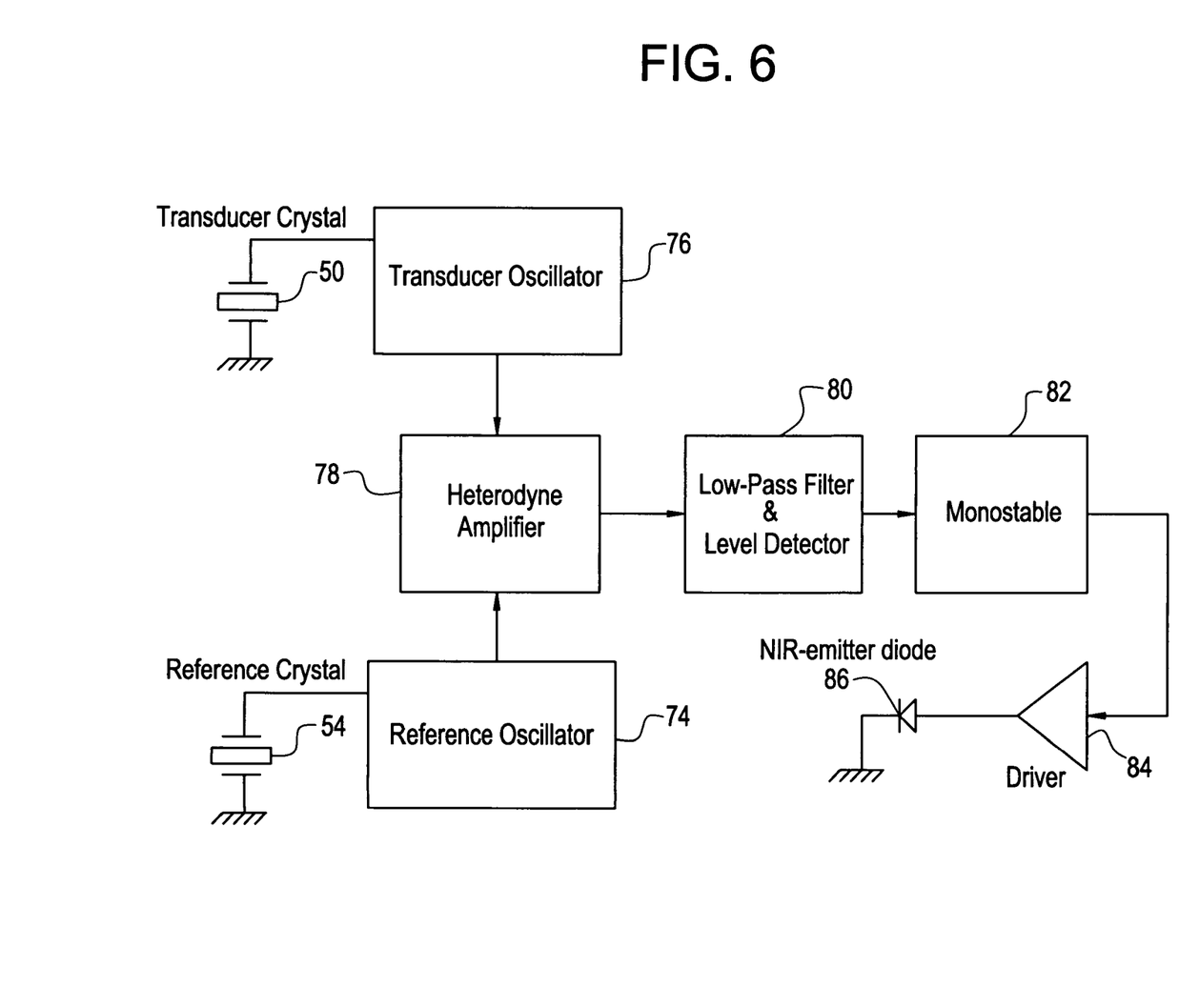
FIG. 6 is a schematic electrical block diagram illustrating a preferred arrangement for measuring a patient pressure parameter in accordance with the invention.

In the preferred embodiment, the sensitivity and long-term stability of the system is maximized using a frequency-coherent detection scheme. As shown in FIG. 6, two identical, yet independent, crystal oscillators are employed. A reference crystal 54 serves a reference oscillator 74 while the transducer crystal 50 serves the transducer oscillator 76. The difference in frequency between the two oscillators is detected using a heterodyne amplifier 78. The difference frequency is ultimately measured and used to compute the pressure applied to the transducer crystal 50. The inherent long-term stability of the quartz crystal-controlled transducer oscillator 76 is augmented by cancellation of drift (thermal, aging, parasitic capacitance, etc.) by the reference oscillator 74.

The output of the heterodyne amplifier 78 is low-pass filtered to obtain the beat-frequency and a level detector with hysteresis 80 is used to derive a digital signal to trigger a monostable multivibrator 82 at the beat frequency. The output of the monostable 82 is used to modulate the NIR-emitter diode 86 via driver 84. The output pulse of the monostable 82 is selected to be as short as feasible to minimize the power consumption of the implant. The system is designed such that lower, more physiological pressures, are associated with lower beat frequencies, again to decrease current consumption. As intracranial pressure rises, the beat frequency increases. The dynamic range of the frequency change is determined by the electromechanical characteristics of the transducer crystal 50 over the operating pressure range. A two-point calibration of the implanted sensor module 14 may be performed at the factory by trimming of the components on the monolithic circuit 58. The minimum on-time pulse width for the NIR-emitter diode 86 is typically limited by the bandwidth of the detector electronics in the external coupling module 20.

Various semiconductor materials are known which are capable of emitting suitable NIR wavelengths. In practice, most are light-emitting diodes (LEDs). The light output intensity is generally proportional to the diode's forward current, and depending on the device, this current can typically range from 20 mA to 1.5 A. Laser diodes tend to have greater optical output but at the expense of higher current requirements and more complicated driver circuitry. High current requirements are not feasible in a miniature implanted device which relies on transcutaneously derived power.

The Vertical Cavity Surface Emitting Laser (VCSEL) provides a high-performance, low-current, high-optical-power solution. In the preferred embodiment, a VCSEL is employed as the NIR-emitter 86, such as a Honeywell SV5637 VCSEL laser diode which produces an 850 nm $1.25$ mW/cm$^2$ output at a mere 10 mA forward current. Furthermore, with the vertical cavity design, the light beam radiates perpendicular to the wafer surface. This facilitates the fabrication of the laser diode and the remainder of the implanted sensor module 14 electronics on a microminiaturized monolithic integrated circuit 58.

Figure 7:
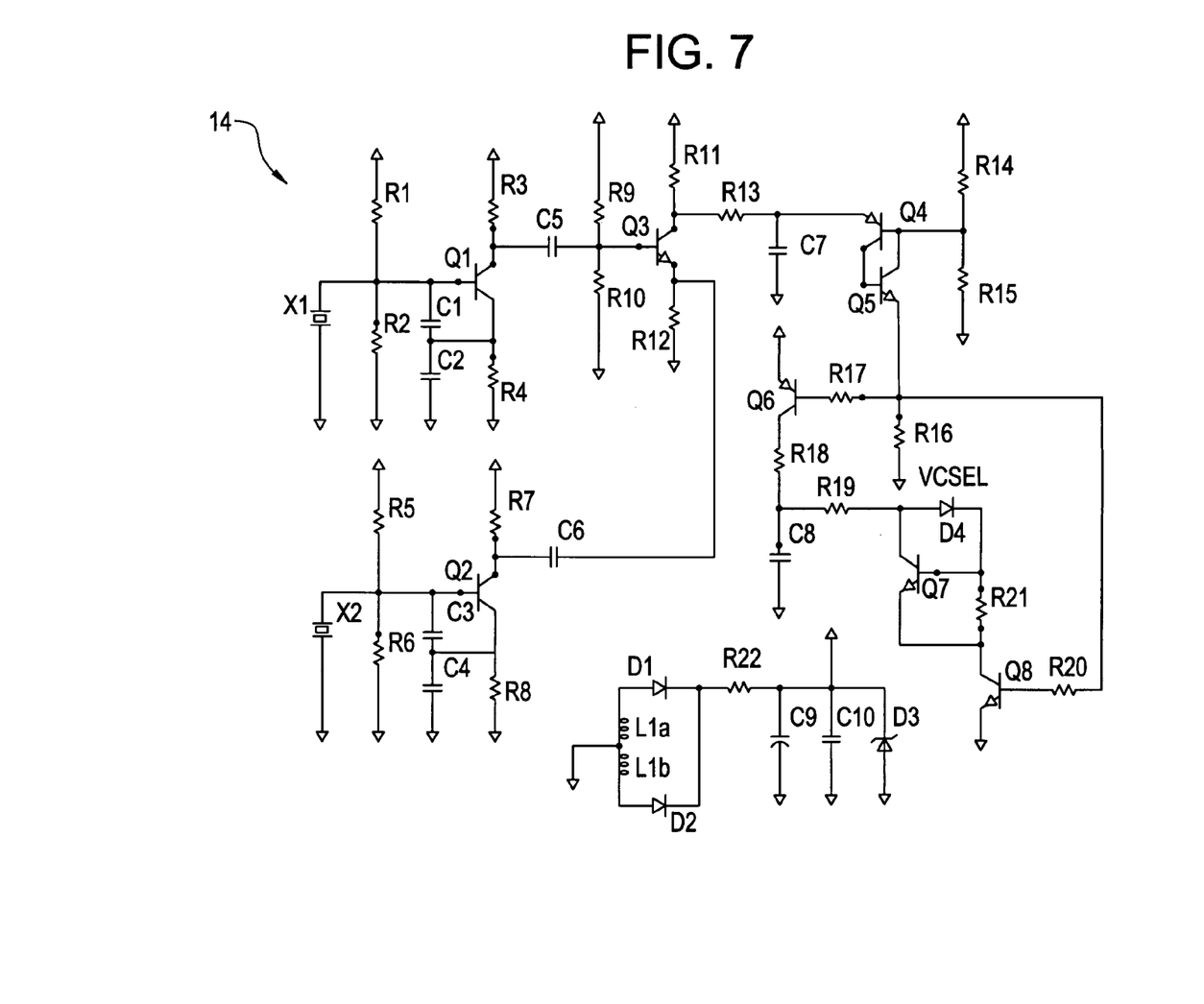
FIG. 7 is an electrical schematic diagram depicting further details of the arrangement shown in FIG. 6.

FIG. 7 depicts a preferred embodiment of the implanted sensor module 14 circuitry. Referring also to FIG. 6, transistors Q1 and Q2 compose two identical Colpitts crystal oscillators, 76 and 74, respectively. X1 is the transducer crystal 50 of FIG. 6 while X2 is the reference crystal 54. X1 and X2 may have the same nominal resonant frequency or may be deliberately tuned with a small offset frequency (see above). Due to these oscillators being essentially identical, the long-term drift, thermal drift, and voltage dependence cancels.

The outputs of each oscillator 76 and 74 are ac-coupled via capacitors C5 and C6 to a heterodyne amplifier 78 (FIG. 6) composed of Q3. The low-pass filtered (R13 and C7) heterodyne signal has a fundamental frequency equal to the frequency difference between the two oscillators 76 and 74. The heterodyne signal is dc-coupled to Q4 and Q5 which are configured as a programmable unijunction-transistor voltage comparator and this serves as a level detector (33). The setpoint of the comparator is determined by the voltage divider composed of R14 and R15.

The output of the unijunction transistor pair provides a digital signal which turns the NIR emitter 86, laser diode D4, on and off at the difference frequency of the two oscillators. A monostable multivibrator 82 (FIG. 6) is composed of Q6, Q8, C8 and associated resistors. When the input voltage is below the unijunction set-point, transistor Q6 conducts, allowing capacitor C8 to charge through resistor R18. The value of C8 is selected to provide adequate charge to drive laser diode D4 at the desired forward current for a nominal minimum period. R18 is selected to provide adequate charging current during one cycle while minimizing current drain on the power supply. Peak laser diode forward current is regulated by Q7. When the voltage-comparator input exceeds the threshold voltage, Q6 turns off to isolate the current drain of the laser diode from the supply rail, while Q8 conducts current from C8 to the laser diode D4. The duration that the laser remains on is determined by the values of C8, R19, and the minimum forward lasing current of D4. Current consumption is minimized by keeping the duty cycle of the laser diode low.

Power to the implanted sensor module 14 is inductively coupled to coil L1 via a time-varying magnetic flux 22 (FIG. 1) which is applied transcutaneously by the complementary external coupling module 20. Coil L1 may be a wire wound as a 'short solenoid' which is embedded in the implant's external housing 40 (FIG. 3), or as in a preferred embodiment, a photochemically-etched metallic spiral on a suitable substrate such as the monolithic circuit 58 (FIG. 4). The induced electromotive force from center-tapped coil L1 is then rectified by diodes D1 and D2, which are ideally of the Schotkey type. This produces a direct current (DC) which is subsequently low-pass filtered by resistor R22 and capacitors C9 and C10 to derive a DC supply voltage. A zener diode D3 across the output is used to suppress voltage transients which might be induced by extraneous magnetic fields, such as from a Magnetic Resonance Imaging (MRI) scanner.

Figure 8:
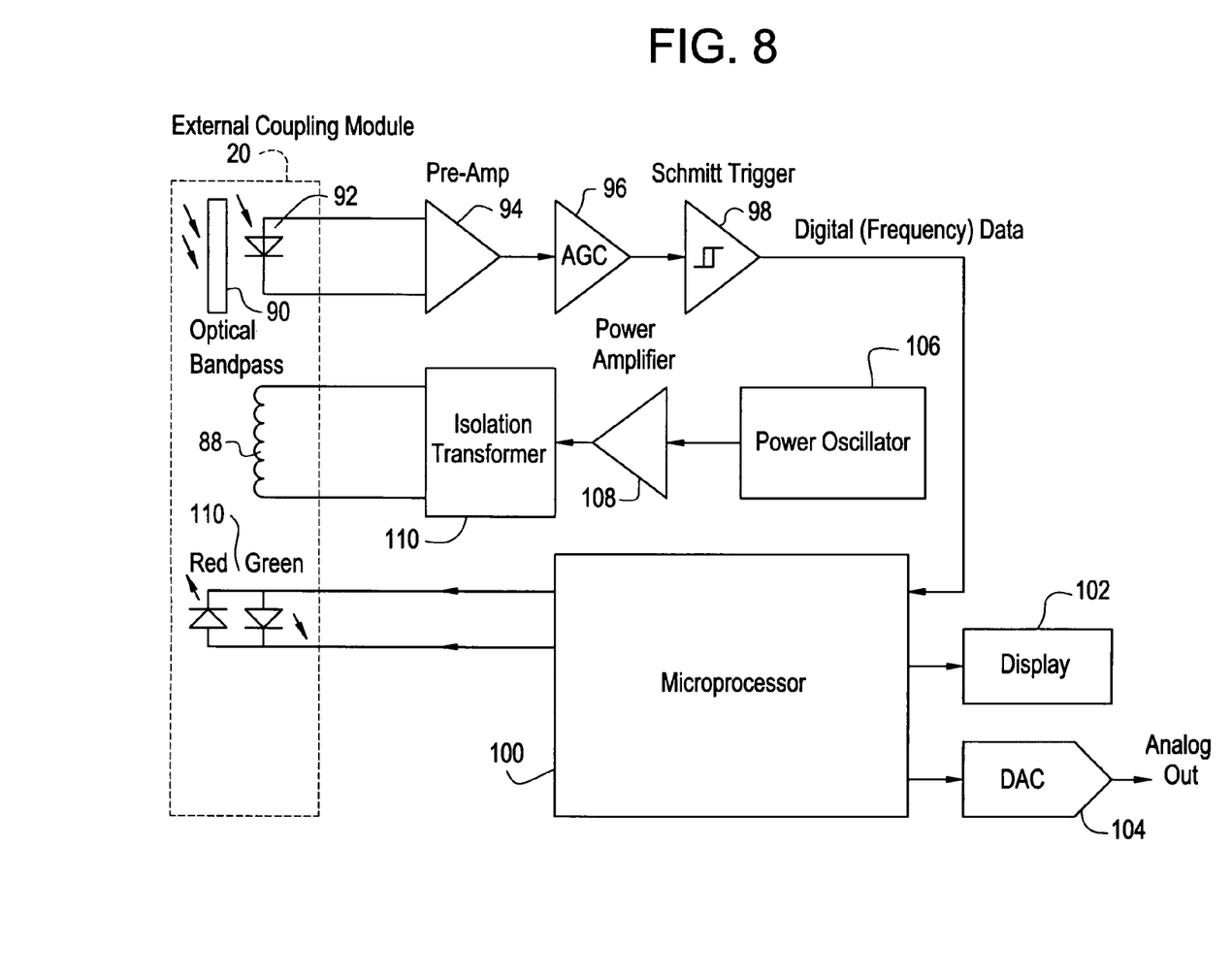
FIG. 8 is a schematic block diagram of the electronics used in the system of the invention which are external to the patient.

External Coupling Module 20 (FIG. 1) and Processing & Display Module 24 (FIG. 1):

Most of the external electronics may be conveniently located in a housing mounted at the bedside of the patient. FIG. 8 depicts a schematic block diagram of the electronics external to the patient. An external coupling module 20 houses electronic components which are necessarily closely associated with the implanted sensor module 14. A single cable (not shown) goes from the external coupling module 20 to the processing and display module 24. This cable is shielded to minimize spurious electromagnetic radiation emission. The external coupling module 20 is placed in proximity to, i.e. over, the implanted sensor module 14 to telemeter the physiological variable 12. The external coupling module 20 may be disc-shaped and contains a coil 88 to deliver inductively-coupled power to the implanted sensor module 14. An optical filter 90 on the undersurface of the external coupling module 20 permits NIR light 18 (FIG. 1) to reach a semiconductor optical detector 92. In a preferred embodiment a photodiode is used. Ideally this device is matched with the NIR emitter 86 such that the peak wavelength sensitivity of photodetector 92 corresponds to that of the NIR emitter 86. Optical signal-to-noise ratio is improved using a narrow bandpass filter 90. Further improvements in SNR may be achieved through biasing of the photodiode. Advanced techniques such as phase-coherent or frequency-coherent detection may be employed. The external coupling module 20 may optionally contain a preamplifier 94 for the photodetector 92. The photodetector 92 signal is further conditioned by an automatic gain control (AGC) amplifier 96. In the preferred embodiment, an edge-detector such as a Schmitt trigger 98 is used to detect the rise and fall of the photodetector 92 output, which in turn correlates with NIR emitter 86 pulse frequency. A microprocessor 100 converts the pulse frequency to a pressure value based on known calibration constants. The microprocessor 100 may then perform any additional signal processing prior to outputting the pressure data either graphically, numerically on a visual display 102, or in analog fashion via digital-to-analog converter 104. A calibrated analog output facilitates connection to existing patient-care monitoring equipment.

A high-frequency oscillator 106 and associated power amplifier 108 provide the necessary drive current to coil 88 to produce the time-varying magnetic flux 22 (FIG. 1) to power the implanted sensor module 14. Isolation transformer 110 provides galvanic isolation between the processing and display module 24 and the patient-connected external coupling module 20.

A visible bi-colored LED 110 mounted on the external coupling module 20 (FIG. 1) casing aids in the positioning of the external coupling module over the implanted sensor module 14. The LED indicates red when power is applied to external coupling module 20 and indicates green when NIR light emission 18 (FIG. 1) is detected from the implanted sensor module 14. Thus, the green LED may be used to aid in positioning of the external coupling module 20 over the implanted sensor module as the NIR emitter 86 (FIG. 6) will only be detected when there is adequate proximity and col-linear alignment of the primary 88 and secondary (L1 of FIG. 7) coils. The outer casing of external coupling module 20 is optically opaque at the NIR emitter 86 wavelength to avoid exposure of medical personnel to the optical radiation. The external coupling module 20 may be held in place by any convenient means, such as with a headband, a stocking cap, or preferably by an articulated arm attached to the bedside.

Each pressure transducer system, e.g. transducer 50 and reference 54 crystal pair, (FIG. 4) is factory calibrated using a two-point calibration. The difference frequency at zero atmospheric pressure is used as a baseline and the difference frequency at a specified physiological extreme, e.g. 100 mmHg, is used to compute the slope of the two-point calibration. These data are then sufficient to compute the actual transducer pressure with high linearity and monotonicity given that the transducer crystal 50 frequency is intrinsically lower than the reference crystal 54 frequency.

The calibration coefficients obtained in the above fashion may be stored electronically in a database accessible from the internet. Upon initialization of the pressure recordings from the transducer, the database may be accessed and the proper calibration coefficients entered into the processing and display module 24. The database may be indexed by patient identifier.

Device Safety:

The VCSEL laser diodes considered for use as the NIR emitter provide a power output of 5 mW or less. The amount of energy absorbed by the overlying tissue would be well below the United States safety standard of 90 mW/cm$^2$ for long-term exposure [5]. Furthermore, the design described inherently has a 'safety interlock' as power is only applied to the implanted sensor module when the external coupling module is held directly over the scalp. The NIR-opaque external coupling module 20 prevents an observer from gazing into the laser beam emanating from the implant. A visible light photo detector may be embedded in the patient-side of the external coupling module 20 to prevent the device from being energized when ambient light is present. This necessitates that the external coupling module be applied to the scalp overlying the implant 14 (FIG. 1) prior to telemetry commencing.

The preferred embodiment described in the foregoing provides a simple and practical means for unidirectional transcutaneous telemetry of a physiological parameter using near infrared light. However, the direction of information travel is immaterial. If both the intracorporeal and extracorporeal devices are equipped with a transceiver (i.e. emitter and detector), then data may flow in bidirectional fashion.

Two different wavelengths of infrared light may be utilized to minimize "crosstalk" during communication between the intra- and extra-corporeal devices. The choice of transmission wavelength is dependent upon the permeability of the tissue at that wavelength and the electrical characteristics of the semiconductor emitter. Appropriate choices could include, but are not limited to, 850 nm and 1050 nm. Because biological tissues tend to scatter incident light in unpredictable fashion, it is conceivable that light from an emitter in either device could be reflected back upon the receiver in that same device. By specifying a particular wavelength for transmission in a given direction, the receivers may be equipped with narrow band-pass filters to selectively respond only to incident light from the intended sender. Furthermore, incorporation of such band-pass filters give the desired effect of excluding ambient light which could adversely affect the signal-to-noise ratio of the communication pathway.

Existing electronic implant devices typically utilize radio frequency (RF) telemetry during application of a strong magnetic field (to actuate a reed switch); narrow bandwidth optical telemetry would markedly reduce or eliminate the susceptibility of these devices to the electromagnetic fields experienced during Magnetic Resonance Imaging.

In an alternative embodiment, the functionality of the implant is maximized by incorporating a microprocessor into the implanted device. While increasing device complexity, it allows for complex data transmission schemes, signal processing within the device, storage and modification of calibration data, and a broader information transmission bandwidth.

Also, the NIR emitter may serve a dual role. Physiological pressures, such as that of cerebrospinal fluid, may be measured using the same infrared emitter as used for the transcutaneous telemetry of data. An optical means of pressure measurement could involve the use of a reflective strip on a distensible membrane which is in contact with the cerebrospinal fluid. The displacement of the membrane as a function of pressure is described by formulas provided in engineering texts [8]. Hence, by measuring the degree of displacement at a given location on the membrane, the applied pressure may be calculated. A portion of the light emitted by the incorporated NIR emitter is bounced off the reflective area of the membrane and the resultant reflection pattern is detected by a linear array of photo detectors such as a charge-coupled device. Alternatively, a diffraction grating may be utilized and the resultant interference pattern analyzed.

The inclusion of a semiconductor temperature sensor within the implant electronics would allow temperature compensation for variations in ambient temperature. This is particularly important with optical pressure transduction schemes utilizing diffraction pattern analysis due to the high sensitivity of such systems to dimensional changes from thermal expansion.

The transcutaneous telemetry of data via infrared light beam serves as the basis for a plethora of applications. This technology may serve as a replacement for existing radio frequency (RF) telemetry systems (incorporated in cardiac pacemakers and neurostimulators) which may be affected by environmental RF energy such as present in MRI scanners.

Furthermore, complex serial data transmission protocols are facilitated by the high bandwidth, allowing many physiological parameters to be transduced simultaneously in real-time.

A logical extension of the technology described herein is incorporation of a photometric system for measuring brain tissue oxygenation. The techniques for spectrophotometric measurement of total hemoglobin, oxyhemoglobin, and deoxyhemoglobin are described in the literature [3]. In summary, tissue absorption at several near infrared wavelengths (e.g. 780 nm, 805 nm, 830 nm) is used to compute the concentration of each chromophore.

Figure 9:
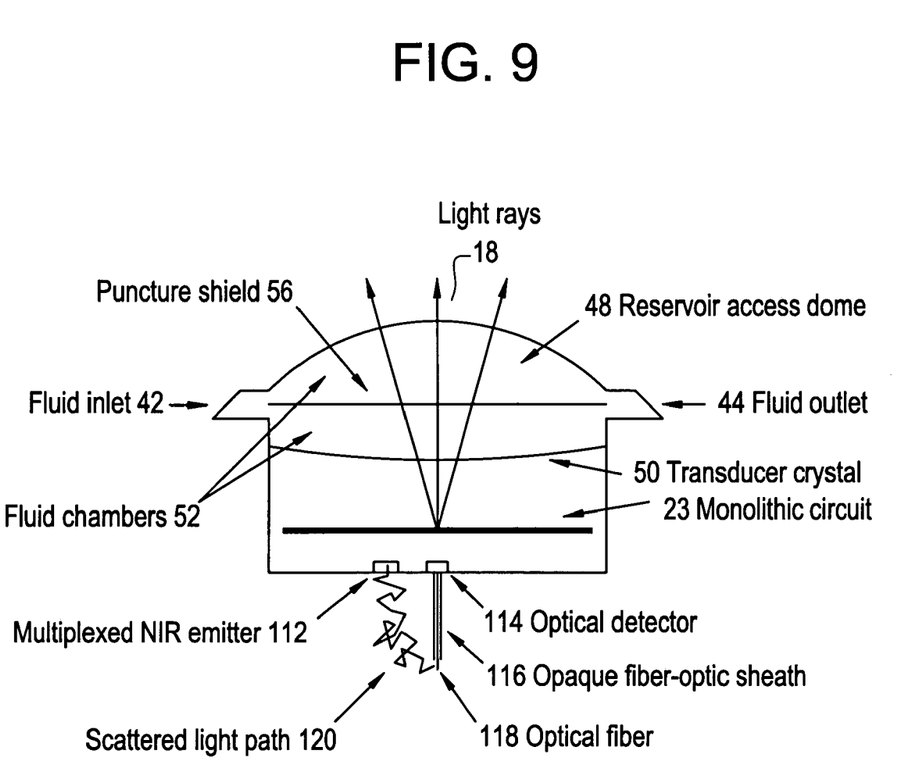
FIG. 9 is a schematic longitudinal cross-section illustrating a sensing device for an embodiment of the invention which is suitable for monitoring brain tissue oxygenation.

An illustrative system for implementing ICP and brain tissue exygenation monitoring is depicted in FIG. 9. Portions of the implant which are identical to that in FIG. 4 are identified by the same reference numeral. In this system, a microprocessor is used within the implanted device to perform data analysis and facilitate bidirectional transcutaneous NIR communication. Separate wavelengths are used for each of the communication send and receive channels.

In FIG. 9, a brain oxygenation sensor is comprised of NIR emitters 112 of the appropriate wavelengths (e.g. 780 nm, 805 nm, 830 nm) which are oriented such that their light beams are directed downward through NIR-transparent windows in the base of the implant housing. Power consumption by the NIR emitters 112 is minimized through multiplexing; briefly turning on each emitter sequentially at a rate fast enough to make the physiological parameter 12 of interest relatively quasistatic. A fiber optic catheter 118 extends from the implant housing into the brain tissue and conveys transmitted NIR light 120 from the multiplexed NIR-emitters 112 back to an optical detector 114 to measure optical absorbance. An optically opaque sheath 116 covers all but a small portion of the tip of the fiber optic catheter 118 such that the light must travel a minimum known distance through the brain tissue. Simultaneous linear equations available in the literature relate the relative absorbance of light at each wavelength to spectrophotometrically calculate the concentration of total hemoglobin, oxyhemoglobin and deoxyhemoglobin. These calculations may be performed by a microprocessor embedded into the implanted device. The microprocessor device also manages asynchronous serial data communications with the extracorporeal monitor via a bi-directional dual-wavelength NIR-telemetric link 18 providing handshaking, sending of the chromophore and ICP readings, and receiving of calibration constants.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

REFERENCES

[1] Delpy, D. T., Cope, M., van der Zee, P., Arridge, S., Wray, S. and Wyatt, J. "Estimation of optical path length through tissue from direct time of flight measurement." Physics, Medicine and Biology 33(12):1433-42, 1988.

[2] Svaasand, L. O. and Ellingsen, R. "Optical properties of brain." Photochemistry and Photobiology, 38(3):293-9, 1983.

[3] Tamura, M. and Tamura, T. "Non-invasive monitoring of brain oxygen sufficiency on cardiopulmonary bypass patients by near-infra-red laser spectrophotometry." Medical and Biological Engineering and Computing 32:S151-6.

[4] Wray, S., Cope, M., Delpy, D. T., Wyatt, J. S. and Reynolds, E. O. R. "Characterization of the near infrared absorption spectra of cytochrome aa3 and hemoglobin for the non-invasive monitoring of cerebral oxygenation." Biochimica et Biophysica Acta 933:184-92, 1988.

[5] American National Standards for the Safe Use of Lasers, American National Standards Institute, Inc., New York, publication Z136.1, 1976.

[6] Owen-Reece, H., Elwell, C. E., Wyatt, J. S. and Delpy, D. T., "The effect of scalp ischaemia on measurement of cerebral blood volume by near-infrared spectroscopy." Physiological Measurements, November, 17(4):279-86, 1996.

[7] Cope, M and Delpy, D. T. "System for long term measurement of cerebral blood and tissue oxygenation on newborn infants by near infrared transillumination." Medicine, Biology, Engineering and Computing, 26(3):289-94, 1988.

[8] Young, W. C., and Budynas, R., *Roark's Formulas for Stress and Strain*, 4$^{th}$ edition, McGraw-Hill, Chapter 10.

The invention claimed is:

1. A system for measuring and converting to an observer intelligible form an internal physiological pressure of a medical patient, comprising:

(a) a patient-implantable sensor module;

(b) an external coupling module positionable externally of the medical patient; and (c) a processing and display module for receiving an output from the coupling module and generating the observer intelligible form indicative of the internal physiological pressure;

(d) the patient-implantable sensor module including:
(1) means for obtaining a measured physiological pressure and providing a digital signal indicative of the measured physiological pressure;
(2) a source of NIR wavelength light;
(3) means for modulating Near infrared (NIR) wavelength light from the source of Near infrared (NIR) wavelength light to incorporate the digital signal and thereby producing a NIR telemetry signal indicative of the measured physiological parameter;
(4) means for directing the NIR telemetry signal through the medical patient's tissues to a point external to the medical patient for coupling with the processing and display module;
(5) a chamber in communication with a bodily fluid of the medical patient, and a deformable diaphragm mounted in the chamber and being deformable as a function of the pressure of the bodily fluid; and means for converting a deformation state of the diaphragm to the digital signal;
(6) wherein the diaphragm comprises a transducer crystal which exhibits a change in oscillation frequency as a function of its deformation;
(7) a monolithic circuit including means for modulating the output of the source of NIR wavelength light as a function of the pressure on the transducer crystal;
(8) wherein the transducer crystal comprises an x-cut quartz crystal, means for resonating the transducer crystal at its fundamental frequency, and means for determining a change in oscillation frequency and utilizing the change in oscillation frequency to convert the deformation state to the digital signal;
(9) wherein the transducer crystal is paired with a nominally identical reference crystal which is not in contact with the bodily fluid, a set of output signals from the transducer crystal and the nominally identical reference crystal, respectively, controlling a transducer oscillator and a reference oscillator; means for detecting and measuring a difference frequency between the transducer oscillator and the reference oscillator; and means for using the difference frequency to compute the pressure applied to the transducer crystal;
(10) wherein the monolithic circuit is positioned between the transducer crystal and the nominally identical reference crystal; and,
(11) wherein the source of NIR wavelength light is a vertical cavity surface emitting laser positioned to transmit NIR radiation through a NIR portal in the transducer crystal; and including means for turning the source of NIR wavelength light on and off at the difference frequency;

(e) the coupling module including means for receiving the NIR telemetry signal which has transited the medical patient tissues and providing a corresponding electrical signal to the processing and display module; and wherein (f) the processing and display module includes means for converting the electrical signal from the coupling module to the observer intelligible form.

2. A system in accordance with claim 1 wherein the patient-implantable sensor further includes an integrated self-sealing chamber adjacent the transducer crystal.

3. A system in accordance with claim 1 wherein the external coupling module includes means for generating a high frequency alternating electromagnetic field for transcutaneous transmittal to the patient-implantable sensor module; and wherein the patient-implantable sensor module includes a means for converting energy in the high frequency alternating electromagnetic field to power for operating the patient-implantable sensor module; and wherein the patient-implantable sensor module is only powered when the high frequency alternating electromagnetic field is present.

4. A system in accordance with claim 3 wherein the sensor module is adapted for measuring pressure in the bodily fluid of the medical patient.

5. A system in accordance with claim 1, wherein the patient-implantable sensor module includes a puncture-resistant shield adjacent the transducer crystal.

6. A system in accordance with claim 1, wherein the NIR portal is generally transparent to NIR wavelength light.

7. A system in accordance with claim 1, wherein the output of the source of NIR wavelength light is frequency modulated.

8. A system in accordance with claim 1, wherein the transducer crystal has a first nominal oscillation frequency no higher than a second nominal oscillation frequency of the reference crystal to ensure that the difference frequency is monotonic.

9. A system in accordance with claim 1, wherein the measured physiological parameter is the intracranial pressure of the medical patient.

10. A system in accordance with claim 1, wherein the measured physiological parameter is a brain tissue oxygenation state of a brain tissue of the medical patient; and wherein the system includes a second source of NIR wavelength light disposed to transmit NIR radiation through the brain tissue; and an optical detector, optically coupled to the second source of NIR wavelength light, for receiving NIR wavelength light scattered by the brain tissue; and means for converting an intensity value of the NIR wavelength light received by the optical detector to a second digital signal for transmission to the external coupling module for display as the observer intelligible form.

11. A system in accordance with claim 1, further including a narrow band-pass optical filter in the optical path of the NIR wavelength light between the patient-implantable sensor module and the external coupling module to improve signal-to-noise ratio.

12. A system in accordance with claim 1 wherein the external coupling module and the patient-implantable sensor module further include sending and receiving means for modulated NIR wavelength light transmission of desired information from the external coupling module to the patient-implantable sensor module, to enable two way communication between the external coupling module and the patient-implantable sensor module.

* * * * *